United States Patent [19]

Stevens

[11] 4,324,785
[45] Apr. 13, 1982

[54] FOOT POWDER

[75] Inventor: Emma S. Stevens, Box 4969, Aspen, Colo. 81611

[73] Assignees: Emma S. Stevens; Stephen A. Holmes, both of Aspen, Colo.

[21] Appl. No.: 151,650

[22] Filed: May 20, 1980

[51] Int. Cl.³ .................... A61K 35/78; A61K 7/035; A61K 9/14

[52] U.S. Cl. ..................................... 424/195; 424/46; 424/69; 426/651

[58] Field of Search ......................... 424/46, 69, 195; 426/638, 640, 651

[56] References Cited

U.S. PATENT DOCUMENTS 60,039  11/1866  Needles ............................... 424/195
97,345  11/1869  Bissell ................................. 424/195
284,629  9/1883  Guillouma .......................... 424/195
324,919  8/1885  Christopher ....................... 424/195

OTHER PUBLICATIONS

Christopher, "School of Natural Healing" Published and Copyrighted by Dr. J. Christopher, Utah (1976) pp. 237–241 and 417–420.

*Primary Examiner*—Donald B. Moyer
*Attorney, Agent, or Firm*—Spencer & Kaye

[57] ABSTRACT

A composition for imparting warmth to the skin, especially to the feet. The composition includes about 30% to about 80% by volume powdered cayenne pepper, about 10% to about 50% by volume powdered ginger, 0 to about 40% by volume powdered mustard and 0 to about 20% by volume of at least one powdered aromatic substance.

8 Claims, No Drawings

FOOT POWDER

BACKGROUND OF THE INVENTION

This invention applies to the field of topical preparations.

One of the major problems experienced by skiers and others who spend long periods of time outdoors in cold weather is that of coldness in the extremities. After exposure to cold temperatures, the feet in particular become painful. Previously, the most common method of preventing cold feet has been to insulate the feet from the environment, such as by wearing insulated boots or additional layers of socks. Insulation, however, can be increased only to a limited degree, consideration being given to the comfort and mobility of the wearer. Further the feet will eventually become cold as the blood vessels of the feet constrict in order to retain heat in the rest of the body. The only solution, then, has been for the skier to return indoors.

Electric boot warmers and socks have also been used to prevent cold feet. These devices are battery powered, which limits their use over extended periods of time. A typical device, an electric heating pad sole for boots, does not provide enough heat for really cold conditions and supplies only short, five-minute bursts of heat, with a maximum cumulative operating time of only 90 minutes before the batteries must be recharged overnight. Use beyond the 90 minutes without recharging can result in permanent damage to the units.

Chemical reactions which release heat have also been used. These reactions, however, fade rapidly and can be dangerous to the skin.

Preparations which provide a sense of warmth to painful areas of the body are well known, and are generally based on counterirritants, substances which produce a superficial irritation in order to reduce irritation in adjacent structures. Such counterirritants commonly used in these preparations include capsicum oleoresin, methyl salicylate, turpentine, mustard, and camphor. A commercially available preparation, for instance, contains capsicum oleoresin, turpentine and petrolatum. These heat-producing preparations are recommended for treatment for muscle pain and arthritis, but are not associated with producing a sense of warmth apart from the treatment of pain.

A composition, known as "outdoor cream" is available for application to the hands and feet. This composition contains water, triethanolamine stearate, propylene glycol, cocoa butter, dimethicone, acetylated lanolin, magnesium stearate, glyceryl stearate, mineral oil, lanolin alcohol, PVP, methyl paraben, propyl paraben, and triclosan.

SUMMARY OF THE INVENTION

It is an object of the present invention to provide a powder suitable for use on the feet, that will provide a feeling of warmth in feet exposed to cold temperature.

It is another object of the present invention to provide a powder which is made of natural and inexpensive materials.

It is a further object of the present invention to provide a powder which is non-toxic.

To achieve these objects and in accordance with its purpose, the present invention provides a composition for imparting warmth when applied to the skin, comprising: about 30% to about 80% by volume powdered cayenne pepper, about 10% to about 50% by volume powdered ginger 0 to about 40% by volume powdered mustard, and 0 to about 20% by volume of at least one powdered aromatic substance.

It is to be understood that both the foregoing general description and the following detailed description are exemplary, but are not restrictive of the invention.

DETAILED DESCRIPTION OF THE INVENTION

The powder prepared according to the present invention will contain, by volume, about 30% to about 80%, and preferably about 30% to about 70%, and most preferably about 40% to about 45% cayenne pepper. Known also as capsicum, cayenne pepper is the dried ripe fruit of *Capsicum frutescens* L., Solanaceae (African Chillies), *Capsicum annuum* L., var conoides Irish (Tobasco Pepper), *Capsicum annuum* var. Longum Sendt (Louisiana Long Pepper), or a hybrid between the Honka variety of Japanese Capsicum and the Old Louisiana Sport Capsicum known as Louisiana Sport Pepper (Fam. Solanaceae). Capsicum, and a constituent thereof, capsaicin, are known counterirritants.

The amount of cayenne pepper in the powder of the present invention is a function of the temperatures at which the powder will be used. Under normal conditions, 0°–30° F., 40–45% cayenne pepper will generally be sufficient. At temperatures of −30°–0° F., 60% cayenne pepper in the composition is preferred, and for use in extreme cold, below −30° F., 80% cayenne pepper is preferred.

Cayenne pepper is available in various pungency ratings depending on the amount of oil present. The cayenne pepper used will generally have a pungency rating of 20 to 40 heat units, preferably 20 or 40. The highest pungency rating, 40, is preferred for the coldest winter weather, and for persons with poor sensitivity and circulation. A product with a pungency rating of 20 or 30 is preferred for warmer spring temperatures and for persons with sensitive feet, even in very cold conditions. The pungency rating affects the perception of warmth provided by the composition more than it affects the amount of cayenne pepper to be used in the composition. Thus, a rating of 20 is perceived as milder than 40, regardless of how much cayenne pepper is used in the composition.

Powdered ginger will be present in the composition of the present invention in an amount of about 10% to about 50%, preferably about 20% to about 50%, and most preferably about 27% to about 32%, by volume. Ginger is the dried rhizome of *Zingiber officinale* Roscoe, Zingiberaceae.

Powdered mustard is an optional component of the composition and may be present in an amount of 0 to about 40%, and preferably is present in an amount of about 3% to about 40%, and more preferably is present at about 20% to about 40% by volume. Both black mustard and white mustard may be used. Black mustard consists of the dried ripe seeds of *Brassica nigra* (L.) Koch or *B. juncea* (L.) Cosson, or varieties of these species. White mustard consists of the dried ripe seeds of *Brassica alba* (L.) Boiss (*Sinapis alba* L.) Cruciferae.

A powdered aromatic substance, or mixtures of aromatic substances may also be added to the present compositions in an amount of up to about 20% by volume total, preferably, about 5% to about 20%. Examples of aromatic substances are clove, also known as caryophillus, which consists of the dried flower buds of *Eugenia* caryophyllata Thunb, (*Caryophyllus aromaticus* L.), Myrtaceae, spearmint, the dried leaves and tops of *Mentha spicata* L. (*M. viridis* L.) Labiatae., and peppermint, the dried leaves and flowering tops of *Mentha piperita* L., Labiatae.

It is believed that in the compositions of the invention, when used as directed, cayenne pepper acts as both a counterirritant and a vasodilator, increasing blood flow in the areas of the skin where applied and thus preventing the feet from becoming cold. Ginger acts as a carrier for the cayenne pepper, generalizing its effect, improving its efficiency, and increasing the duration of its effect. The presence of mustard increases the speed with which the cayenne pepper and ginger work, shortening the time necessary for the composition to provide the full foot heating effect, from, for instance, one to four hours, to ¼ to about one hour. The aromatics act as mild stimulants, and increase the effect of warmth of the compositions.

In preferred embodiments of the invention, fillers are not added to the compositions. Fillers tend to absorb the oil present in the active ingredients, and thereby block the absorption of the ingredients by the skin and the effect produced thereby.

The compositions of the present invention may be prepared by thoroughly blending all ingredients in powdered form.

Since the compositions of the invention lose potency upon exposure to the air and moisture, it is preferred that the composition be hermetically sealed in packets containing enough powder for one application. It is suggested that such packets contain about 1.8 to 2.0 grams of powder, which for most people is enough for application to the toe area of one foot during the low temperatures of mid-winter. During the spring, when temperatures are less severe, as little as 0.2 grams will be sufficient for many people. Use of an excess of powder is to be avoided.

For best results, one packet of the composition is sprinkled in the toe area of each sock at least two hours before the user goes outside in cold weather. The user puts on the sock and rubs the toe area until the powder is evenly distributed. Since the skin on the top of the feet is very sensitive, application to this area will often provide a warming effect that will be too intense for most people. Application to the toe area will generally adequately warm the rest of the foot.

In general, first-time users of the composition should begin by applying about 0.2 grams of the composition to each foot, and increasing the amount until a determination of the amount needed to produce comfortable warmth is made. This amount will generally be between 0.2 and 2.0 grams. For many people, one foot is more sensitive than the other and will require less powder. Usually the sensitive foot will correspond directly to the dominant hand.

Persons with sensitive skin will initially use about half the recommended amount of the composition, and gradually increase the amount used until the feet are comfortably warm. Persons who will not be outdoors most of the day should use less of the composition. If the composition is to be used on consecutive days, less powder should be used each day.

The feet should be washed thoroughly and the socks changed after returning indoors after a day's activity. If the feet become excessively irritated from the use of the composition, they should be washed in cold water with soap, and a sunburn lotion applied to relieve the symptoms.

The following examples are given by way of illustration to further explain the principles of the invention. These examples are merely illustrative and are not to be understood as limiting the scope and underlying principles of the invention in any way.

EXAMPLE 1

A composition for use at temperatures of 0° to 32° F. (−17.8° to 0° C.) is prepared by blending powders of the following ingredients:

| Ingredient | % by Volume |
| --- | --- |
| Cayenne Pepper (pungency rating = 40) | 43% |
| Ginger | 29% |
| Black Mustard | 21% |
| Clove | 7% |

The blended powder was measured into 1.87 gram portions and hermetically sealed in plastic, foil, or packets made of any other suitable material or composition of materials.

EXAMPLE 2

Another composition for use at 0° to 32° F. is prepared by blending the following ingredients:

| Ingredient | % by Volume |
| --- | --- |
| Cayenne Pepper (pungency rating = 20) | 45% |
| Ginger | 30% |
| White Mustard | 25% |

The blended powder is measured into 3.9 gram portions, sufficient for application to two feet, and hermetically sealed in plastic, foil, or packets made of any other suitable material or composition of materials.

EXAMPLE 3

A composition for use at temperatures of −30° to 0° F. (−34.4° to −17.8° C.) is prepared by blending the following ingredients:

| Ingredient | % by Volume |
| --- | --- |
| Cayenne Pepper (pungency rating = 20) | 60% |
| Ginger | 27% |
| White Mustard | 10% |
| Clove | 3% |

EXAMPLE 4

Another composition for use at −30° to 0° F. is prepared by blending the following ingredients:

| Ingredient | % by Volume |
| --- | --- |
| Cayenne Pepper (pungency rating = 30) | 65% |
| Ginger | 35% |

EXAMPLE 5

A composition for use at temperatures below −30° F. (−34.4° C.) is prepared by blending the following ingredients:

| Ingredient | % by Volume |
| --- | --- |
| Cayenne Pepper (pungency rating = 40) | 80% |
| Ginger | 10% |
| Black Mustard | 7% |
| Clove | 3% |

EXAMPLE 6

Another composition for use below −30° F. is prepared by blending the following ingredients:

| Ingredient | % by Volume |
| --- | --- |
| Cayenne Pepper (pungency rating = 20) | 80% |
| Ginger | 12% |
| Clove | 5% |
| Spearmint | 3% |

It will be understood that the above description of the present invention is susceptible to various modifications, changes and adaptations, and the same are intended to be comprehended within the meaning and range of equivalents of the appended claims.

What is claimed is:

1. A powder composition for imparting warmth when applied to living, human skin, comprising:
   about 30% to about 80%, by volume, powdered cayenne pepper;
   about 10% to about 50% by volume, powdered ginger;
   about 3% to about 40% by volume, powdered mustard; and
   0 to about 20%, by volume, of at least one powdered aromatic substance selected from the group consisting of clove, spearmint and peppermint.

2. A composition according to claim 1, wherein said cayenne pepper is present at about 30% to about 70% by volume, said ginger is present at about 20% to about 50% by volume, and said aromatic substance is present at about 5% to about 20% by volume.

3. A composition according to claim 2, wherein said cayenne pepper is present at about 40% to about 45% by volume, said ginger is present at about 27% to about 32% by volume, and said mustard is present at about 20% to about 40% by volume.

4. A composition according to claim 1 wherein the cayenne pepper has a pungency rating of 20 to 40.

5. A composition according to claim 1, wherein cayenne pepper is present at about 43% by volume, ginger is present at about 29% by volume, mustard is present at about 21% by volume, and clove is present at about 7% by volume.

6. A composition according to claim 1, wherein said cayenne pepper is present at about 30% to about 80% by volume, said ginger is present at about 20% to about 50% by volume, and said mustard is present at about 20% to about 40% by volume.

7. A composition according to claim 6, wherein said cayenne pepper is present at about 60% to about 80% by volume.

8. A method for imparting warmth to a living human foot comprising applying to said foot about 0.2 to about 2.0 grams of a powder according to claim 1.

* * * * *